(12) United States Patent
Matsutani et al.

(10) Patent No.: US 9,168,210 B2
(45) Date of Patent: Oct. 27, 2015

(54) HAIR COSMETIC

(71) Applicant: Henkel AG & Co. KGaA, Duesseldorf (DE)

(72) Inventors: Akira Matsutani, Chiba (JP); Masaki Kawai, Tokyo (JP); Shoji Machida, Tokyo (JP)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/297,865

(22) Filed: Jun. 6, 2014

(65) Prior Publication Data

US 2014/0283315 A1    Sep. 25, 2014

Related U.S. Application Data

(63) Continuation of application No. PCT/JP2012/075409, filed on Oct. 1, 2012.

(30) Foreign Application Priority Data

Nov. 30, 2011    (JP) ................. 2011-261725

(51) Int. Cl.
  *A61Q 5/06* (2006.01)
  *A61K 8/04* (2006.01)
  *A61K 8/31* (2006.01)
  *A61Q 5/10* (2006.01)
  *A61K 8/86* (2006.01)
  *A61K 8/34* (2006.01)
  *A61K 8/41* (2006.01)

(52) U.S. Cl.
  CPC ................. *A61K 8/042* (2013.01); *A61K 8/046* (2013.01); *A61K 8/31* (2013.01); *A61K 8/342* (2013.01); *A61K 8/416* (2013.01); *A61K 8/86* (2013.01); *A61Q 5/10* (2013.01); *A61K 2800/48* (2013.01)

(58) Field of Classification Search
  CPC .......... A61Q 5/10; A61K 8/342; A61K 8/416
  USPC ...................... 8/405, 477, 580, 606; 424/70.1
  See application file for complete search history.

(56) References Cited

U.S. PATENT DOCUMENTS

| 6,916,432 | B2 | 7/2005 | Matsuo et al. |
| 7,122,062 | B2 | 10/2006 | Yamashita et al. |
| 7,842,100 | B2 | 11/2010 | Matsunaga et al. |
| 2004/0103488 | A1* | 6/2004 | Yamashita et al. ................. 8/406 |

FOREIGN PATENT DOCUMENTS

| JP | 2007-217292 A | 8/2007 |
| JP | 2010-077084 A | 4/2010 |
| WO | 2009/122505 A1 | 10/2009 |

OTHER PUBLICATIONS

PCT International Search Report (PCT/JP2012/075409) dated Apr. 12, 2012.

* cited by examiner

*Primary Examiner* — Eisa Elhilo
(74) *Attorney, Agent, or Firm* — P. Scott Smith

(57) ABSTRACT

A problem to be solved by the present invention is to provide a hair cosmetic which can be easily applied to the hair uniformly, and at the same time, does not drip from the hair, does not spatter when applied to the hair, and does not dirty the surrounding, clothing, the skin or the like. The present invention relates to a hair cosmetic comprising (A) a cationic surfactant, (B) a nonionic surfactant, (C) a higher alcohol, (D) an oil having an IOB value of 0.1 or lower, and (E) water, which is used after being mixed with a gas to be thickened.

7 Claims, No Drawings

HAIR COSMETIC

FIELD OF THE INVENTION

The present invention relates to a hair cosmetic which is used after being mixed with a gas to be thickened.

BACKGROUND ART

A hair cosmetic is used for a variety of purposes, and is used as a hair styling agent for the purpose of hair styling property, a hair treatment agent for the purpose of treatment property, a permanent agent for the purpose of imparting a permanent wave to the hair, a hair dye or a decolorant for the purpose of changing the color of the hair, or the like. Among these hair cosmetics, liquid, creamy, gel-like, spray and foam-like forms are predominant.

These hair cosmetics are used by being applied to the hair, and are required to be capable of being easily applied to the hair uniformly. At the same time, it is also desired that a hair cosmetic does not drip from the hair, does not spatter when applied to the hair, and does not dirty the surrounding, clothing, the skin or the like.

Among the various forms, a liquid hair cosmetic has the characteristic that it is easily applied to the hair, but has a defect that it drips easily. On the other hand, a creamy hair cosmetic has the characteristic that it drips with difficulty, but it has a defect that it is spread with difficulty when applied to the whole hair and hairs are entangled since the cosmetic has high viscosity. A spray hair cosmetic has a defect that spattering to the surrounding or clothing is caused and a specific container equipped with a nozzle which discharges the cosmetic in a spray form is required. Since a foam-like hair cosmetic is foamy, it is applied to the hair in the state where it is diluted with the air. For this reason, in order to make an effective component act at a sufficient concentration, it is required that the concentration of the effective component is enhanced in advance. Furthermore, the hair cosmetic has a defect that a specific container equipped with a nozzle which discharges the hair cosmetic in a foam-like form is required.

Therefore, a hair cosmetic has a problem to be solved that it can be easily applied to the hair uniformly and, at the same time, it does not drip from the hair, does not spatter when applied to the hair, and does not dirty the surrounding, clothing, the skin or the like.

Concerning the problem of a hair cosmetic, for example, in the field of a hair dye or a decolorant aiming at changing the color of the hair, a hair cosmetic which is thickened into a gel by mixing a first agent containing a surfactant in a high concentration with a second agent containing a specific amount of water (e.g. Patent Document 1), and a hair cosmetic which is thickened by mixing a first agent containing an anionic polymer with a second agent containing an alkali agent by utilizing a nature that the anionic polymer is thickened under an alkaline condition (e.g. Patent Document 2) are known.

Patent Document 1 describes a hair dye composition which is gelled and thickened by mixing a first agent containing a surfactant in a high concentration with a second agent containing a specific amount of water. In this hair dye composition, when the first agent containing a surfactant in a high concentration contains water in an amount exceeding a given amount, the first agent itself is thickened, and therefore a lower alcohol such as ethanol or isopropanol is contained in the first agent in an amount around 5 to 30%. As described above, since the first agent contains a large amount of the lower alcohol and the surfactant, the cost may be increased, the hair may be defatted excessively by hair dyeing, the hair may be damaged and dried, and the hair may come to have a rough feeling. Further, since the amount of water contained in the first agent is small, a precipitate may be generated and storage stability may be deteriorated, depending on the solubility of the dye.

Patent Document 2 describes a two-pack type oxidation hair dye and a two-pack type decolorant which are thickened by mixing a first agent containing an alkali agent with a second agent containing an anionic polymer such as an acrylic acid-methacrylic acid copolymer as a thickener. In these two-pack type oxidation hair dye and two-pack type decolorant, usually the first agent and the second agent can be easily mixed with each other since both of them are liquid, and the resultant mixed liquid has such a viscosity that it is easily applied to the hair by the effect of the anionic polymer. However, the use of the anionic polymer may make the hair creaky and rough.

Furthermore, a foamy hair cosmetic which is obtained by shaking a first agent and a second agent upon mixing, thereby giving a foamy agent (e.g. Patent Document 3) is also known. Patent Document 3 describes a hair cosmetic which is a hair dye or a decoloring and destaining agent, that is formulated into a foamy dosage form by a foaming operation of foaming a first agent and a second agent by shaking upon use. This hair cosmetic is in a foamy dosage form, and is applied to the hair in the state where the hair cosmetic is diluted with the air. For this reason, in order to obtain a decoloring effect or a hair dyeing effect which is comparable with that of a liquid or gel-like hair cosmetic, the concentration of an alkali agent or a dye should be increased in advance since the hair cosmetic is applied to the hair after being diluted with the air. In addition, the hair cosmetic contains the alkali agent or the dye in high concentrations, which results in that breakage of the hair or damage of the hair may become severe.

PRIOR ART DOCUMENTS

Patent Documents

Patent Document 1: JP-A-55-49308
Patent Document 2: JP-A-11-199454
Patent Document 1: JP-A-2011-93819

SUMMARY OF THE INVENTION

Problems to be Solved by the Invention

The present invention aims to solve the aforementioned problem, and an object of the present invention is to provide a hair cosmetic which can be easily applied to the hair uniformly and, at the same time, does not drip from the hair, does not spatter when applied to the hair, and does not dirty the surrounding, clothing, the skin or the like.

Solutions to the Problems

The present inventors found that the problem is solved by a hair cosmetic comprising (A) a cationic surfactant, (B) a nonionic surfactant, (C) a higher alcohol, (D) an oil having an IOB value of 0.1 or lower, and (E) water, which is used after being mixed with a gas to be thickened, resulting in completion of the present invention.

Specific aspects of the hair cosmetic of the present invention include the following:

(1) A hair cosmetic comprising (A) a cationic surfactant, (B) a nonionic surfactant, (C) a higher alcohol, (D) an oil having an IOB value of 0.1 or lower, and (E) water, which is used after being mixed with a gas to be thickened;

(2) The hair cosmetic according to (1), wherein the ratio of the total content of the surfactants of (A) and (B) relative to the content of (C) the higher alcohol is 0.6 to 2.5;

(3) The hair cosmetic according to (1) or (2), further comprising (F) a water-soluble polyhydric alcohol;

(4) The hair cosmetic according to any one of (1) to (3), wherein the hair cosmetic is a hair dye or a decolorant;

(5) The hair cosmetic according to (4), wherein the hair cosmetic is a two-pack type hair dye or decolorant comprising a first agent containing an alkali agent and a second agent containing an oxidizing agent;

(6) The hair cosmetic according to (5), wherein (A) to (E) are contained in the second agent;

(7) The hair cosmetic according to any one of (1) to (6), wherein the viscosity before being mixed with a gas is 8000 mPa·s or less, the viscosity after being mixed with a gas is 2000 mPa·s to 12000 mPa·s, and the hair cosmetic is thickened at a thickening rate of 10% or more by being mixed with a gas; and (8) A method of using a hair cosmetic, in which the hair cosmetic defined in (7) is thickened by being mixed with a gas, and applied to the hair.

Effects of the Invention

According to the present invention, there is obtained a hair cosmetic which can be easily applied to the hair uniformly and, at the same time, does not drip from the hair, does not spatter when applied to the hair, and does not dirty the surrounding, clothing, the skin or the like.

Further, when the hair cosmetic of the present invention is a hair dye or a decolorant, in addition to the aforementioned effect, an effect is obtained that the hair after treatment is easy to comb and comes to have a smooth touch feeling. Furthermore, when the hair cosmetic of the present invention is a hair dye or a decolorant which is used by mixing two agents with each other, in addition to the aforementioned effect, an effect is obtained that a first agent and a second agent are easily mixed with each other, and the hair after treatment is easy to comb and comes to have a smooth touch feeling.

MODES FOR CARRYING OUT THE INVENTION

Embodiments of the present invention will be explained below.

The hair cosmetic of the present invention is not particularly limited as far as it is a hair cosmetic which is used after being mixed with a gas to be thickened, and may be a variety of hair cosmetics such as a hair styling agent for the purpose of hair styling property, a hair treatment agent for the purpose of treatment property, a permanent agent for imparting a permanent wave to the hair, or a hair dye or a decolorant for the purpose of changing the color of the hair.

The hair cosmetic of the present invention is preferably a hair dye or a decolorant, although not particularly limited. This is because a large amount of a hair cosmetic should be applied to the whole hair in the case of the hair dye or the decolorant, and therefore a hair cosmetic which does not spatter when applied to the hair and does not dirty clothing or the like is particularly strongly demanded.

Furthermore, as a hair cosmetic, there are a hair cosmetic which is used as a one-pack type and a hair cosmetic which is used by mixing two agents with each other, and both of them are included in the present invention. For example, as a hair dye or a decolorant, there are a hair dye or a decolorant which is used as a one-pack type to give a hair dyeing effect and a decoloring effect, and a hair dye or a decolorant which is used by mixing a first agent containing an alkali agent and a second agent containing an oxidizing agent with each other to give a hair dyeing effect and a decoloring effect. Both of them are included in the hair cosmetic of the present invention. Herein, although the hair cosmetic of the present invention is not particularly limited, a hair cosmetic which is used by mixing two agents with each other is preferable since the hair cosmetic of the present invention is a hair cosmetic which is used after being mixed with a gas to be thickened and a gas can be mixed at the same time as the mixing of the two agents.

The hair cosmetic of the present invention contains (A) a cationic surfactant, (B) a nonionic surfactant, (C) a higher alcohol, (D) an oil having an IOB value of 0.1 or lower, and (E) water, and is used after being mixed with a gas to be thickened.

The hair cosmetic of the present invention contains (A) the cationic surfactant in order to be thickened by being mixed with a gas. By (A) the cationic surfactant, fine air bubbles entrapped in the thickened hair cosmetic are stabilized and the viscosity of the thickened hair cosmetic is maintained. Furthermore, by the addition of (A) the cationic surfactant to the hair cosmetic, a conditioning effect can be imparted to the hair.

Preferred examples of the cationic surfactant include alkyltrimethyl ammonium chloride and alkyltrimethyl ammonium bromide for the purpose of achieving better thickening. For example, ethyl sulfuric acid lanolin fatty acid aminopropylethyl dimethylammonium, alkyltrimethyl ammonium chloride, octadecyl ammonium chloride, octyl dihydroxyethylmethyl ammonium chloride, dialkyl (12-15)dimethyl ammonium chloride, dialkyl (14-18)dimethyl ammonium chloride, dicocoyl dimethyl ammonium chloride, distearyl dimethyl ammonium chloride, dicetyl dimethyl ammonium chloride, di(polyoxyethylene)oleyl methyl ammonium chloride, stearyl dihydroxyethyl betaine sodium chloride, stearyl dimethylbenzyl ammonium chloride, stearyl trimethyl ammonium chloride, cetyl trimethyl ammonium chloride, cetyl pyridinium chloride, benzalkonium chloride, benzethonium chloride, polyoxyethylene(1) polyoxypropylene(25) diethylmethyl ammonium chloride, myristyl dimethylbenzyl ammonium chloride, methyl benzethonium chloride, lauryl trimethyl ammonium chloride, lauryl pyridinium chloride, alkyl isoquinolinium bromide, stearyl trimethyl ammonium bromide, cetyl trimethyl ammonium bromide, lauryl trimethyl ammonium bromide, stearyl trimethyl ammonium saccharine and cetyl trimethyl ammonium saccharine can be mentioned. For the purpose of achieving further better thickening with the hair cosmetic, alkyltrimethyl ammonium chloride is more preferable, and stearyl trimethyl ammonium chloride and cetyl trimethyl ammonium chloride are particularly preferable. The hair cosmetic of the present invention may contain these cationic surfactants alone, or may contain a combination of two or more of the cationic surfactants.

The content of the cationic surfactant is preferably 0.1% by weight or more, and more preferably 0.3% by weight of more in order to impart a sufficient conditioning effect to the hair. On the other hand, since a preferable viscosity and good stability of the hair cosmetic are obtained, the content is preferably 5% by weight or less, and more preferably 3% by weight or less.

In addition, in the case of a hair cosmetic which is used as a one-pack type, the cationic surfactant is preferably contained in the aforementioned content relative to the whole amount of the hair cosmetic. In the case of a hair cosmetic which is used by mixing two agents with each other, the cationic surfactant is contained in at least one of the agents. In this case, the content of the cationic surfactant in a mixed liquid obtained by mixing a first agent and a second agent with each other is preferably the aforementioned content relative to the whole amount of the mixed liquid.

The hair cosmetic of the present invention contains (B) the nonionic surfactant in order to give a viscosity that makes it easy to apply the hair cosmetic which is thickened by mixing with a gas and to obtain stability of the hair cosmetic.

In the present invention, examples of the nonionic surfactant include polyoxyethylene isostearyl ether, polyoxyethylene isocetyl ether, polyoxyethylene octyl dodecyl ether, polyoxyethylene oleyl ether, polyoxyethylene oleyl cetyl ether, polyoxyethylene stearyl ether, polyoxyethylene cetyl ether, polyoxyethylene cetostearyl ether, polyoxyethylene tridecyl ether, polyoxyethylene butyl ether, polyoxyethylene behenyl ether, polyoxyethylene myristyl ether, polyoxyethylene lauryl ether, polyoxyethylene octyl phenyl ether, polyoxyethylene dinonyl phenyl ether and polyoxyethylene nonyl phenyl ether. In order to give better stability of the hair cosmetic and a viscosity that makes it further easier to apply the hair cosmetic which is thickened by mixing with a gas, the nonionic surfactant preferably contains polyoxyethylene alkyl ether, and polyoxyethylene stearyl ether, polyoxyethylene cetyl ether and polyoxyethylene cetostearyl ether are particularly preferable. The hair cosmetic of the present invention may contain these nonionic surfactants alone, or may contain a combination of two or more of the nonionic surfactants.

The content of the nonionic surfactant is preferably 0.1% by weight or more, and more preferably 1.0% by weight or more in order to impart better stability of a hair cosmetic and a viscosity that makes it easy to apply the hair cosmetic which is thickened by being mixed with a gas. On the other hand, for better stability of the hair cosmetic, the content is preferably 10% by weight or less, and more preferably 8% by weight or less.

In addition, in the case of a hair cosmetic which is used as a one-pack type, the nonionic surfactant is preferably contained in the aforementioned content relative to the whole amount of the hair cosmetic. In the case of a hair cosmetic which is used by mixing two agents with each other, the nonionic surfactant is contained in at least one of the agents. In this case, the content of the nonionic surfactant in a mixed liquid obtained by mixing a first agent and a second agent with each other is preferably the aforementioned content relative to the whole amount of the mixed liquid.

The HLB of the nonionic surfactant is preferably 10 or higher, and more preferably 12 or higher in order to obtain better emulsifiability.

The hair cosmetic of the present invention contains (C) a higher alcohol in order to assist emulsifiability of a surfactant and impart a viscosity that makes it easy to apply the hair cosmetic which is thickened by being mixed with a gas.

In the present invention, examples of the higher alcohol include alcohols having 8 to 24 carbon atoms such as lauryl alcohol, myristyl alcohol, cetanol, stearyl alcohol, behenyl alcohol, cetostearyl alcohol, isostearyl alcohol, oleyl alcohol, hexyldecanol, and octyldodecanol. Among them, higher alcohols having 12 to 22 carbon atoms are preferable because the effect of assisting emulsifiability of a surfactant is better and they give a viscosity that makes it easy to apply the hair cosmetic which is thickened by being mixed with a gas. Higher alcohols having 14 to 18 carbon atoms are more preferable. Among the higher alcohols having 14 to 18 carbon atoms, myristyl alcohol, cetanol, stearyl alcohol, and cetostearyl alcohol are preferable, and cetanol is more preferable.

The hair cosmetic of the present invention may contain these higher alcohols alone, or may contain a combination of two or more of the higher alcohols.

The content of the higher alcohol is preferably 0.1% by weight or more, and more preferably 0.8% by weight or more. By increasing the content of the higher alcohol, stability of a hair cosmetic can be improved, and excellent operability, dyeability, and fastness can be obtained. On the other hand, since operability of mixing and application can be improved, the content is preferably 10% by weight or less, and more preferably 4% by weight or less.

The ratio of the total content of the surfactants of (A) and (B) (the content of (A) the cationic surfactant+the content of (B) the nonionic surfactant) relative to the content of (C) the higher alcohol can be calculated by the equation of ((A)+(B))/(C). In order to make an agent have a viscosity that makes the agent easier to mix, the ratio is preferably 0.6 or more, and more preferably 1.0 or more. On the other hand, in order to thicken a hair cosmetic to a viscosity that makes the hair cosmetic easier to apply by mixing with a gas, the ratio is preferably 2.5 or less, and more preferably 2.0 or less.

In addition, in the case of a hair cosmetic which is used as a one-pack type, the higher alcohol is preferably contained in the content and/or the ratio in the aforementioned range relative to the whole amount of the hair cosmetic. In the case of a hair cosmetic which is used by mixing two agents with each other, the higher alcohol is contained in at least one of the agents. In this case, the content of the higher alcohol in a mixed liquid obtained by mixing a first agent and a second agent with each other is preferably the aforementioned content relative to the whole amount of the mixed liquid. Furthermore, in a mixed liquid obtained by mixing a first agent and a second agent with each other, the ratio of the total content of the surfactants of (A) and (B) relative to the content of (C) the higher alcohol is preferably in the aforementioned range. In a hair dye or a decolorant, when the higher alcohol has been saponified with an alkali or the like, the content of the higher alcohol refers to the content obtained by conversion in terms of a pure higher alcohol.

The hair cosmetic of the present invention contains (D) an oil having an IOB value of 0.1 or lower in order to make the touch feeling of the hair good and impart a viscosity that makes it easy to apply the hair cosmetic which is thickened by being mixed with a gas.

Herein, the IOB (Inorganic Organic Balance) value means an IOB value in an organic conceptual diagram.

The organic conceptual diagram was proposed by Atsushi Fujita. In the diagram, the characteristic of an organic compound is divided into organicity mainly based on the number of carbon atoms (covalent property) and inorganicity based on the nature and tendency of a substituent (ion binding property), and an organic compound is positioned on an orthogonal coordinate named as an organic axis and an inorganic axis so as to understand the outline of the nature of the organic compound. Details thereof are explained in, for example, "Pharmaceutical Bulletin", vol. 2, 2, pp. 163-173 (1954), "Area of Chemistry" vol. 11, 10, pp. 719-725 (1957), and "Fragrance Journal", vol. 50, pp. 79-82 (1981). Specifically, numerical values as an organicity value (OV) and an inorganicity value (IV) are imparted to each of the carbon atoms and substituents of an organic compound, and these numerical values are used to obtain the sum of the organicity value and the inorganicity value from the structure of a certain molecule. Then, these values are plotted on an orthogonal coordinate named as an organic axis and an inorganic axis to give the organic conceptual diagram. This organic conceptual diagram is also shown in, for example, "Organic Conceptual Diagram—Basic and Application—" (authored by Yoshio Koda, Sankyo Publishing Co., Ltd., 1984).

Here, the IOB value in this organic conceptual diagram refers to the ratio of the inorganicity value (IV) relative to the organicity value (OV), that is, "inorganicity value (IV)/organicity value (OV)".

In the present invention, examples of the oil having an IOB value of 0.1 or lower include hydrocarbon oils such as polybutene, squalane, liquid paraffin, and vaseline; and ester oils such as octyldodecyl myristate, isocetyl isostearate, cetyl palmitate, isocetyl stearate, and hexyldecyl isostearate. Among them, hydrocarbon oils are preferable because the touch feeling of the hair can be made better and they give a viscosity that makes it easy to apply the hair cosmetic which is thickened by being mixed with a gas. Particularly, squalane (IOB=0), vaseline (IOB=0), and liquid paraffin (IOB=0) and the like are more preferable. The hair cosmetic of the present invention may contain these oils having an IOB value of 0.1 or lower alone, or may contain a combination of two or more of the oils.

The content of the oil having an IOB value of 0.1 or lower is not particularly limited, and the oil can be contained in any amount. In order to impart a viscosity that makes it easier to apply the hair cosmetic which is thickened by being mixed with a gas, the content is preferably 10% by weight or less, and more preferably 5% by weight or less. In addition, since the touch feeling of the hair can be made better, the content is preferably 0.1% by weight or more.

In addition, in the case of a hair cosmetic which is used as a one-pack type, the oil is preferably contained in the aforementioned content relative to the whole amount of the hair cosmetic. In the case of a hair cosmetic which is used by mixing two agents with each other, the oil having an IOB value of 0.1 or lower is contained in at least one of the agents. In this case, the content of the oil having an IOB value of 0.1 or lower in a mixed liquid obtained by mixing a first agent and a second agent with each other is preferably the aforementioned content relative to the whole amount of the mixed liquid.

The hair cosmetic of the present invention contains (E) water in order to dissolve or disperse other blending components to stably blend them in the hair cosmetic.

The water is not particularly limited, and purified water is preferable. The content of water is the remainder of the whole amount excluding predetermined amounts of various blending components, and is appropriately adjusted by the kind, content and the like of the components. In order to sufficiently dissolve or disperse the other blending components to more stably blend them in the hair cosmetic, the content of water is preferably 10% by weight or more, and more preferably 30% by weight or more.

In addition, in the case of a hair cosmetic which is used as a one-pack type, the water is preferably contained in the aforementioned content relative to the whole amount of the hair cosmetic. In the case of a hair cosmetic which is used by mixing two agents with each other, water is contained in at least one of the agents. In this case, the content of water in a mixed liquid obtained by mixing a first agent and a second agent with each other is preferably the aforementioned content relative to the whole amount of the mixed liquid.

On the other hand, when the hair cosmetic of the present invention is a two-pack type hair dye, in order to improve solubility of the dye contained in the first agent, prevent generation of a precipitate and improve storage stability, the first agent contains water preferably in an amount of 10% by weight or more, and more preferably 30% by weight or more.

The hair cosmetic of the present invention preferably contains (F) a water-soluble polyhydric alcohol in addition to the essential components because the effect of preventing precipitation of other components is high and storage stability of the hair cosmetic can be more enhanced. Furthermore, when the hair cosmetic is a hair dye or a decolorant, the hair cosmetic preferably contains (F) a water-soluble polyhydric alcohol since penetration of a hair dyeing or decoloring component into the hair can be promoted. When the hair cosmetic is a hair cosmetic which is used by mixing two agents with each other, mixability of two agents can be more improved by addition of the water-soluble polyhydric alcohol to the hair cosmetic.

In the present invention, examples of the water-soluble polyhydric alcohol include ethylene glycol, propylene glycol, glycerin, polyethylene glycol, ethylene glycol monoethyl ether, and ethylene glycol monobutyl ether. Among these polyhydric alcohols, propylene glycol, glycerin and polyethylene glycol are preferable since they can more effectively prevent precipitation of other components. Further, when the hair cosmetic is a hair dye or a decolorant, propylene glycol, glycerin and polyethylene glycol are preferable since sufficient penetration of a hair dyeing or decoloring component into the hair is achieved. The hair cosmetic of the present invention may contain these polyhydric alcohols alone, or may contain a combination of two or more of the polyhydric alcohols.

The content of the water-soluble polyhydric alcohol is preferably 0.1% by weight or more, and more preferably 0.5% by weight or more. This is because precipitation of other components can be more effectively prevented and storage stability of the hair cosmetic is more improved by increasing the content of the water-soluble polyhydric alcohol. On the other hand, when the hair cosmetic is a hair dye, in order to obtain good dyeability, the content is preferably 20% by weight or less, and more preferably 10% by weight or less.

In addition, in the case of a hair cosmetic which is used as a one-pack type, the water-soluble polyhydric alcohol is preferably contained in the aforementioned content relative to the whole amount of the hair cosmetic. In the case of a hair cosmetic which is used by mixing two agents with each other, the water-soluble polyhydric alcohol is contained in at least one of the agents. In this case, the content of the water-soluble polyhydric alcohol in a mixed liquid obtained by mixing a first agent and a second agent with each other is preferably the aforementioned content relative to the whole amount of the mixed liquid.

The hair cosmetic of the present invention is a hair cosmetic which is used after being mixed with a gas to be thickened. "Being mixed with a gas to be thickened" means that the viscosity after being mixed with a gas is higher as compared with the viscosity before being mixed with a gas.

Measurement of the viscosity is performed by measuring the viscosity after 1 minute from 30 rotations of a No. 4 rotor at 25° C. using a B-type viscometer TVB-10 manufactured by Toki Sangyo Co., Ltd.

The viscosity before being mixed with a gas is preferably 8000 mPa·s or lower, and more preferably 6000 mPa·s or lower for ease of mixing. Furthermore, the viscosity after being mixed with a gas is preferably 2000 mPa·s or higher, and more preferably 4000 mPa·s or higher in order to prevent dripping. The viscosity after being mixed with a gas is preferably 12000 mPa·s or lower, and more preferably 10000 mPa·s or lower for applicability to the hair and spreadability of the hair cosmetic.

In the hair cosmetic of the present invention, it is preferable that the hair cosmetic which has been thickened by being mixed with a gas is thickened preferably at a thickening rate of 10% or more as compared with the hair cosmetic before mixing.

The dosage form of the hair cosmetic of the present invention is not particularly limited as far as the viscosity is increased by being mixed with a gas as compared with the viscosity before being mixed with a gas, and the hair cosmetic before being mixed with a gas and the hair cosmetic after being mixed with a gas are preferably liquid, creamy or gel-like. Herein, the hair cosmetics before and after being mixed with a gas may be in the same dosage form, or different dosage forms. From the viewpoint that the hair cosmetic spatters with difficulty and drips with difficulty, the hair cosmetic after being mixed with a gas preferably becomes creamy or gel-like.

Herein, in the case of a hair cosmetic which is used by mixing two agents with each other, "being mixed with a gas to be thickened" means that the viscosity of a mixed liquid after mixing of two agents with each other and mixing with a gas is higher as compared with both of the viscosity of a first agent before being mixed with a gas and the viscosity of a second agent before being mixed with a gas. Furthermore, in this case, both of the viscosity of a first agent before being mixed with a gas and the viscosity of a second agent before being mixed with a gas are preferably the aforementioned viscosity before being mixed with a gas. In addition, a mixed liquid is preferably thickened at the thickening rate in the aforementioned range relative to both of the viscosity of a first agent before being mixed with a gas and the viscosity of a second agent before being mixed with a gas.

Further, in the case of a hair cosmetic which is used by mixing two agents with each other, "being mixed with a gas to be thickened" means that the viscosity of a mixed liquid after mixing of two agents with each other and mixing with a gas is higher as compared with the viscosity of a mixed liquid in the case where two agents are mixed with each other without being mixed with a gas. In this case, the hair cosmetic is preferably thickened so that the viscosity of a mixed liquid after mixing of two agents with each other and mixing with a gas becomes higher by 20% or more, and preferably 50% or more as compared with the viscosity of a mixed liquid in the case where two agents are mixed with each other without being mixed with a gas. This is because two agents are easily mixed with each other, and after being mixed with a gas, the hair cosmetic drips with difficulty and good applicability is obtained. In addition, in this case, the mixed liquid obtained by mixing two agents with each other without being mixed with a gas is obtained by, for example, gently stirring two agents using a glass bar so as not to be mixed with a gas.

Furthermore, the dosage form of the hair cosmetic of the present invention is not particularly limited as far as the viscosity of a mixed liquid after mixing of two agents with each other and mixing with a gas is higher as compared with both of the viscosity of a first agent before being mixed with a gas and the viscosity of a second agent before being mixed with a gas, and a first agent and a second agent before being mixed with a gas and the hair cosmetic after being mixed with a gas are preferably liquid, creamy or gel-like. Herein, the first agent and the second agent before being mixed with a gas and the hair cosmetic after being mixed with a gas may be in the same dosage form, or different dosage forms. From the viewpoint that a hair cosmetic spatters with difficulty and drips with difficulty, the hair cosmetic after being mixed with a gas more preferably becomes creamy or gel-like. In addition, from the viewpoint of ease of mixing, at least one of the first agent and the second agent before mixing is more preferably liquid.

In the present invention, when the hair cosmetic is a hair cosmetic which is used by mixing two agents with each other, the components of (A) to (E) are preferably contained together in at least one of the agents. When the hair cosmetic is a hair dye or a decolorant which is used by mixing two agents with each other, it is more preferable that a first agent contains an alkali agent and a second agent contains an oxidizing agent. Further, the components of (A) to (E) are preferably contained together in the second agent containing an oxidizing agent.

When the hair cosmetic of the present invention is a hair dye or a decolorant, in order to enhance activation of an oxidizing agent, swelling of the hair and penetration of a dye into the hair, the hair cosmetic preferably contains an alkali agent. In the present invention, examples of the alkali agent include aqueous ammonia, alkanolamines such as monoethanolamine (MEA), diethanolamine (DEA), triethanolamine (TEA), 2-amino-2-methyl-1-propanol (AMP), 2-amino-2-methyl-1,3-propanediol (AMPD), tetrakis(2-hydroxyisopropyl)ethylenediamine (TE), and monoisopropanolamine (MIPA), sodium hydroxide, and potassium hydroxide. Aqueous ammonia and monoethanolamine are preferable because better hair dyeing and decoloring effects are obtained and, in respect of odor, monoethanolamine is more preferable. The hair cosmetic of the present invention may contain these alkali agents alone, or may contain a combination of two or more of the alkali agents.

Since the oxidizing agent can be sufficiently activated to promote the effect, the content of the alkali agent is preferably 0.1% by weight or more, and more preferably 1% by weight or more. On the other hand, since breakage of the hair can be more suppressed, the content is preferably 20% by weight or less, and more preferably 10% by weight or less.

In the case of a hair cosmetic which is used as a one-pack type, the alkali agent preferably has the content in the aforementioned range relative to the whole amount of the hair cosmetic. In the case of a hair cosmetic which is used by mixing two agents with each other, the alkali agent is contained in a first agent. In this case, the content of the alkali agent in the first agent is preferably the content in the aforementioned range relative to the whole amount of the first agent.

When the hair cosmetic of the present invention is a hair dye or a decolorant, the hair cosmetic preferably contains an oxidizing agent in order to obtain decoloring and hair dyeing effects. In the present invention, as the oxidizing agent, publicly known oxidizing agents can be widely used except for ammonium salts. Examples thereof include hydrogen peroxide, sodium perborate, potassium perborate, sodium percarbonate, and sodium bromate (these are blended in the form of an aqueous solution or as a raw material). Since the decoloring and hair dyeing effects are high, hydrogen peroxide is preferable. Hydrogen peroxide is preferably uses as a 10 to 35% by weight aqueous solution. The hair cosmetic of the present invention may contain these oxidizing agents alone, or may contain a combination of two or more of the oxidizing agents.

Since sufficient decoloring and hair dyeing effects are obtained, the content of the oxidizing agent is preferably 0.01% by weight or more, and more preferably 0.1% by weight or more. On the other hand, since breakage of the hair can be suppressed and irritation on the scalp can be alleviated, the content is preferably 10% by weight or less, and more preferably 6% by weight or less.

In addition, in the case of a hair cosmetic which is used as a one-pack type, the oxidizing agent is preferably contained in the aforementioned content relative to the whole amount of the hair cosmetic. In the case of a hair dye and a decolorant which are used by mixing two agents with each other, the oxidizing agent is contained in a second agent. In this case, the content of the oxidizing agent in the second agent is preferably the content in the aforementioned range relative to the whole amount of the second agent.

The hair cosmetic of the present invention can contain other components such as a dye, other surfactants, a buffer, an antioxidant, a sequestering agent, a stabilizer, and a cationic polymer in an appropriate combination as far as the effect of the present invention is not deteriorated.

The hair cosmetic of the present invention, when it is a hair dye, contains a dye in order to dye the hair. In the present invention, as the dye, publicly known oxidation dyes and direct dyes which are used in the field of hair dye can be widely used. When the hair cosmetic of the present invention is a hair dye which is used by mixing two agents with each other, a first agent contains the dye.

Examples of the oxidation dye include 5-amino o-cresol, 5-amino o-cresol sulfate, 2,4-diaminophenol chloride, toluene-2,5-diamine chloride, p-phenylenediamine chloride, N-phenyl p-phenylenediamine chloride, m-phenylenediamine chloride, o-aminophenol, N-phenyl p-phenylenediamine acetate, 2,6-diaminopyridine, 2,6-diaminopyridine sulfate, 1,5-dihydroxy naphthalene, diphenylamine, toluene-2,5-diamine, toluene-3,4-diamine, α-naphthol, p-aminophenol, p-phenylenediamine, p-methylaminophenol, hydroquinone, pyrogallol, N-phenyl p-phenylenediamine, phloroglucin, m-aminophenol, m-phenylenediamine, gallic acid, o-aminophenol sulfate, o-chloro-p-phenylenediamine sulfate, 4,4'-diaminodiphenylamine sulfate, toluene-2,5-diamine sulfate, p-aminophenol sulfate, p-phenylenediamine sulfate, p-methylaminophenol sulfate, 1-hydroxyethyl-4,5-diaminopyrazole sulfate, 2-(2-hydroxyethyl)-1,4-phenylene diammonium sulfate, 2-methyl resorcinol, m-aminophenol sulfate and m-phenylenediamine sulfate, and resorcin. The hair cosmetic of the present invention may contain these oxidation dyes alone, or may contain a combination of two or more of the oxidation dyes.

Examples of the direct dye include 2-amino-4-nitrophenol, 2-amino-5-nitrophenol, nitro-p-phenylenediamine chloride, nitro-p-phenylenediamine, p-nitro-o-phenylenediamine, 2-amino-5-nitrophenol sulfate, nitro-p-phenylenediamine sulfate, p-nitro-o-phenylenediamine sulfate, p-nitro-m-phenylenediamine sulfate, 1-amino-4-methylamino anthraquinone, 1,4-diamino anthraquinone, picramic acid, sodium picramate, and 2-((2-nitrophenyl)amino)ethanol. The hair cosmetic of the present invention may contain these direct dyes alone, or may contain a combination of two or more of the direct dyes. In addition, the hair cosmetic of the present invention may further contain the direct dyes in addition to the oxidation dyes.

Since fastness to hair washing of the oxidation dye is higher as compared with fastness to hair washing of the direct dye, it is preferable that only the oxidation dye is used, or the oxidation dye and the direct dye are used in combination as the dye.

The hair cosmetic of the present invention may contain, in addition to the surfactants mentioned above, other surfactants, that is, an anionic surfactant, an amphoteric surfactant and the like as far as the effect of the present invention is not deteriorated. The hair cosmetic of the present invention may contain other surfactants alone, or may contain a combination of two or more of the surfactants, and the content thereof is not particularly limited as far as the content is a sufficient amount for attaining the object of addition.

When the hair cosmetic of the present invention is a hair dye or a decolorant, the hair cosmetic preferably contains, as a buffer, an ammonium salt such as hydrogen ammonium carbonate or ammonium chloride, or a carbonate such as potassium carbonate or sodium carbonate. When the hair cosmetic of the present invention is a hair dye or a decolorant which is used by mixing two agents with each other, it is preferable that a first agent contains the buffer.

When the hair cosmetic of the present invention is a hair dye, the hair cosmetic may contain a low-molecular alcohol such as ethanol or isopropanol in order to more improve solubility of a dye. When the hair cosmetic of the present invention is a hair dye which is used by mixing two agents with each other, it is preferable that a first agent contains the low-molecular alcohol such as ethanol or isopropanol.

The hair cosmetic of the present invention may contain an antioxidant such as a sulfite, ascorbic acid or an ascorbate, and a sequestering agent such as an edetate in order to improve stability. When the hair cosmetic of the present invention is a hair dye or a decolorant which is used by mixing two agents with each other, it is preferable that a first agent contains the antioxidant and/or the sequestering agent.

When the hair cosmetic of the present invention contains an oxidizing agent, it is preferable that the hair cosmetic contains a publicly known stabilizer which has previously been used in a hair dye or a decolorant in order to stabilize the oxidant agent. Examples of the stabilizer include phosphoric acid, pyrophosphoric acid, trisodium phosphate, sodium pyrophosphate, acetanilide, sodium stannate, hydroxyethanediphosphonic acid, and phenoxyethanol. The hair cosmetic may contain these stabilizers alone, or may contain a combination of two or more of the stabilizers. When the hair cosmetic of the present invention is a hair cosmetic which is used by mixing two agents with each other, it is preferable that an agent containing the oxidizing agent contains the stabilizer.

The content of the stabilizer is not particularly limited as far as it is an amount with which the oxidizing agent is stabilized. The blending amount of the stabilizer is preferably 0.00005% by weight or more, and more preferably 0.0001% by weight or more. On the other hand, the blending amount is preferably 5% by weight or less, and more preferably 2% by weight or less.

In addition, in the case of a hair cosmetic which is used as a one-pack type, the stabilizer is preferably contained in the aforementioned content relative to the whole amount of the hair cosmetic. In the case of a hair cosmetic which is used by mixing two agents with each other, the content of the stabilizer in a mixed liquid obtained by mixing a first agent and a second agent with each other is preferably the aforementioned content relative to the whole amount of the mixed liquid.

The hair cosmetic of the present invention may contain a cationic polymer in order to impart a hair protection and softening effect.

Herein, the cationic polymer refers to a polymer having a cation group or a group which can be ionized to a cation group, and also includes a polymer which is cationic as a whole. That is, examples of the cationic polymer include a polymer containing an amino group or an ammonium group on a side chain of a polymer chain, or an aqueous solution of a polymer containing a diallyl quaternary ammonium salt as a constituent unit, for example, a cationized cellulose derivative, cationized starch, a cationized guar gum derivative, a polymer or a copolymer of a diallyl quaternary ammonium salt, and a quaternized polyvinylpyrrolidone derivative. Among them, a polymer or a copolymer of a diallyl quaternary ammonium salt is preferable. Examples of the diallyl quaternary ammonium salt polymer include polydimethylmethylenepiperidinium chloride, a dimethyldiallylammonium chloride-acrylic acid copolymer, and a dimethyldiallylammonium chloride-acrylamide-acrylic acid copolymer.

The content of the cationic polymer is not particularly limited, but it is preferably 0.01% by weight or more, and more preferably 0.1% by weight or more. On the other hand, the content is preferably 3% by weight or less, and more preferably 1% by weight or less.

In addition, in the case of a hair cosmetic which is used as a one-pack type, the cationic polymer is preferably contained in the aforementioned content relative to the whole amount of the hair cosmetic. In the case of a hair cosmetic which is used by mixing two agents with each other, the content of the cationic polymer in a mixed liquid obtained by mixing a first agent and a second agent with each other is preferably the aforementioned content relative to the whole amount of the mixed liquid.

The hair cosmetic of the present invention can contain, in addition to the components mentioned above, other publicly known components such as a hair protecting agent, a flavoring agent, a coloring matter, an ultraviolet absorbing agent, a stabilizer, a penetrant, a wetting agent, and a hair growing agent, if necessary, in an appropriate combination as far as the effect of the present invention is not deteriorated.

The hair cosmetic of the present invention can be produced by dissolving the components in water. The hair cosmetic can be produced by blending, warming, stirring and mixing a part of components, and thereafter cooling the mixture, adding remaining components, and mixing them, if necessary. When the hair cosmetic of the present invention is a hair cosmetic which is used by mixing two agents with each other, a first agent and a second agent can be produced by a publicly known method similarly to the above.

It is more preferable that aqueous phase components which have been warmed and uniformly dissolved are added to oil phase components which have been warmed and uniformly dissolved, and the components are mixed to form a gel-like structure in order to thicken the hair cosmetic by mixing with a gas.

The hair cosmetic of the present invention is a hair cosmetic containing the aforementioned components, and is used after being mixed with a gas to be thickened. Herein, "used after being mixed with a gas to be thickened" refers to that the viscosity of the hair cosmetic of the present invention is increased by being mixed with a gas.

In the present invention, the gas is not particularly limited as far as it is in a gaseous state under the condition where it is mixed with the hair cosmetic of the present invention, and for example, the air or nitrogen existing in the atmosphere is preferable.

In the present invention, a method for mixing with a gas is not particularly limited as far as it is a method by which a hair cosmetic is thickened by being mixed with a gas. For example, a method of mixing the hair cosmetic with a gas by stirring them using a tool such as a brush or a whisk, or a method of mixing the hair cosmetic in a container with a gas by shaking the container can be used. Alternatively, a mixing method using a mechanical force such as a mixer can also be used. In respect of cost and simplicity, the method of mixing the hair cosmetic in a container with a gas by shaking the container is preferable.

In the present invention, the container for mixing the hair cosmetic with a gas is not particularly limited, and a container is preferable in which a gas exists in an upper space on the liquid surface when it is filled with a liquid and the gas existing in the upper space and the liquid in the container are mixed with each other by shaking the container. For example, a bottle-like container and a jar container are preferable because they are easily shaken with a hand and a hair cosmetic which has been thickened by being mixed with a gas is easily taken out.

In the case of a hair cosmetic which is used by mixing two agents with each other, a method of placing two agents filled in separate containers into one container, and mixing the agents with a gas for use is preferable. For example, by transferring one of the agents into a container containing the other agent, closing the container with a lid, and shaking the container with a hand, two agents can be mixed, and at the same time, the agents can be mixed with a gas in the container to thicken the hair cosmetic. In the case of a hair dye or a decolorant which is used by mixing two agents with each other, immediately before use, a first agent and a second agent can be mixed with each other, and at the same time, the agents can be mixed with a gas to thicken the hair cosmetic.

By mixing the hair cosmetic of the present invention with a gas, the gas entrapped during preparation of the hair cosmetic forms fine air bubbles in the preparation. Since the hair cosmetic of the present invention can be stabilized without breaking the air bubbles, the hair cosmetic can be thickened by being mixed with a gas. Particularly, the hair cosmetic of the present invention preferably has a liquid crystal structure in order to achieve better thickening. In this case, the whole system does not have to have a liquid crystal structure, and the ratio of liquid crystal in the system is not particularly defined as far as the necessary property is obtained.

In the hair cosmetic of the present invention, after the hair cosmetic is thickened by being mixed with a gas, it is preferable that the thickening is continued preferably for about 30 minutes or longer, and more preferably for about 60 minutes or longer. This is because this gives better applicability and a liquid is more difficult to drip during application to the hair.

After the hair cosmetic of the present invention is thickened by being mixed with a gas, the thickened hair cosmetic can be used as a variety of hair cosmetics by a normal application method. For example, in the case of a hair styling agent, after the hair styling agent is mixed with a gas in a container containing the hair cosmetic by shaking the container to be thickened, the thickened hair styling agent can be applied to the whole head hair or partially applied thereto to fix the hair or change the gloss, touch feeling, texture or the like of the hair. In the case of a hair treatment agent, similarly, the thickened hair treatment agent can be applied to the whole hair to impart luster, softness and moisture to the head hair. Also in the case of a hair dye or a decolorant, the thickened hair dye or decolorant can be applied to the whole hair to dye or decolor the hair. Herein, as a method of application, a method of application using a tool such as a paint brush or a brush, a method of application with hand, a method of application with hand wearing a glove, and a method of application by discharging the hair cosmetic on the hair with an applicator can be appropriately used without particular limitation. It is preferable to apply the hair cosmetic with hand utilizing dexterity of the hand. When the hair cosmetic is a hair dye or a decolorant, a method of applying the hair cosmetic with hand wearing a glove so as not to dirty the hand is preferable because the hair cosmetic can be applied more easily and uniformly.

The amount of application to the hair can be appropriately set as required.

For example, in the case of a hair dye or a decolorant which is used by mixing two agents with each other, for the whole head with the hair length of around 30 cm, usually, the amount of a first agent is around 20 to 60 g and that of a second agent is around 30 to 100 g, and preferably the amount of a first agent is around 25 to 40 g and that of a second agent is around 50 to 80 g. The mixing ratio between the first agent and the second agent can be appropriately adjusted, and the ratio is 1:0.5 to 1:5, and more preferably 1:1 to 1:3.

The decoloring or hair dyeing time is appropriately selected according to the application amount, kind and amount of an alkali agent, and the desired degree of decoloration or hair dyeing, and examples thereof include 5 minutes or longer, preferably 5 to 50 minutes, more preferably 10 to 45 minutes, and usually up to around 40 minutes.

After the decoloring or hair dyeing time has elapsed, the cosmetic is appropriately washed away and the hair is dried.

Examples

A decolorant and a hair dye which are used by mixing two agents with each other, being one aspect of the present invention, will be explained below with reference to examples, but the present invention is not limited by these examples. In the following examples, the content is in "% by weight."

A first agent and a second agent were prepared by a conventional method according to components and contents described in the following tables.

The resulting first agent and second agent were mixed with each other immediately before use at the designated mixing ratios described in the tables. For the mixing, the prepared first agent and second agent were placed into one container, the container was closed with a lid, and the container was strongly shaken at room temperature to mix the agents, and the mixture was sufficiently stirred until unevenness disappeared.

The prepared decolorant and hair dye were evaluated by evaluation methods of 1 to 7 shown below. The resulting evaluation results of respective examples and comparative examples are shown in Tables 1 to 4. Furthermore, viscosities of a first agent, a second agent and a mixed liquid of Examples 3, 4, 6, 9, and 13 to 15 and Comparative Example 3 are shown in Table 5.

1. Dyeability

In tap water was immersed 2 g of a 100% silver hair bundle (human hair) for 1 hour and the bundle was dried over 23 hours. The hair bundle after being repeatedly subjected to this step five times was used as a hair bundle A for a test.

A first agent and a second agent were mixed with a gas (air) according to the designated mixing ratio to obtain a mixed liquid. Then, 5 g of this mixed liquid was applied to 2 g of the hair bundle A for a test with hand wearing a glove. Then, after the bundle was allowed to stand at 30° C. for 30 minutes, the bundle was washed with water, shampooed, and dried with hot air. Concerning the hair bundle A for a test after drying, dyeability was evaluated visually based on the following criteria.

Excellent: There is no unevenness and the bundle is uniformly dyed.

Acceptable: There is slight unevenness and the dyeing is nonuniform.

Poor: There is unevenness and the bundle is not uniformly dyed.

2. Decoloring Property

In tap water was immersed 2 g of a black hair bundle (human hair) for 1 hour and the bundle was dried over 23 hours. The hair bundle after being repeatedly subjected to this step five times was used as a hair bundle B for a test.

A first agent and a second agent were mixed with each other as described above according to the designated mixing ratio to obtain a mixed liquid. Then, 5 g of this mixed liquid was applied to 2 g of the hair bundle B for a test with hand wearing a glove. Then, after the bundle was allowed to stand at 30° C. for 30 minutes, the bundle was washed with water, shampooed, and dried with hot air. Concerning the hair bundle B for a test after drying, the decoloring property was evaluated visually based on the following criteria.

Excellent: There is no unevenness and the bundle is uniformly decolored.

Acceptable: There is slight unevenness and the decoloring is nonuniform.

Poor: There is unevenness and the bundle is not uniformly decolored.

3. Touch Feeling

After 4 g of a black hair bundle (human hair) was immersed in purified water in which 3% of 28% aqueous ammonia, 6% of 35% hydrogen peroxide, and 0.2% of disodium edetate had been dissolved for 30 minutes, the bundle was washed with water and dried over 24 hours. Then, this was immersed in tap water for 1 hour and dried over 23 hours. The hair bundle after being repeatedly subjected to this step five times was used as a hair bundle C for a test.

A first agent and a second agent were mixed with a gas according to the designated mixing ratio to obtain a mixed liquid. Then, 10 g of this mixed liquid was applied to 4 g of the hair bundle C for a test with hand wearing a glove. Then, after the bundle was allowed to stand at 30° C. for 30 minutes, the bundle was washed with water, shampooed, and dried with hot air. Concerning the hair bundle C for a test after drying, the touch feeling was evaluated by ease of combing based on the following criteria.

Excellent: Combing is very easy and the hair is smooth, being good.

Good: Combing is not obstructed and the hair is smooth.

Acceptable: Combing is difficult and is slightly obstructed.

Poor: Combing is very difficult and is considerably obstructed.

4. Applicability

A first agent and a second agent were mixed with a gas at a predetermined ratio to obtain a mixed liquid. Then, 80 g of the mixed liquid was applied to the whole head of a commercially available wig with hand wearing a glove, and applicability was evaluated based on the following criteria.

Excellent: The mixed liquid is applicable to the whole head without any problem.

Good: The mixed liquid is spreadable with difficulty as compared with the above, but is applicable to the whole head without any problem.

Acceptable: The mixed liquid is partially spread unevenly.

Poor: The mixed liquid cannot be applied to the whole hair because the quantity is insufficient.

5. Mixability and Thickening Property

A first agent and a second agent were mixed with each other at a predetermined ratio and the viscosity of the mixture after 1 minute at 30 rotations of a No. 4 rotor was measured at 25° C. using a B-type viscometer TVB-10 manufactured by Toki Sangyo Co., Ltd. Mixability and the thickening property thereupon were evaluated based on the following criteria.

Excellent: The agents can be easily mixed and the viscosity of the mixed liquid is higher than both the viscosities of the first agent and the second agent.

Good: The agents can be mixed with difficulty as compared with the above but can be mixed without any problem, and the viscosity of the mixed liquid is higher than both the viscosities of the first agent and the second agent.

Acceptable: The viscosity of the mixed liquid is higher than either the viscosity of the first agent or that of the second agent.

Poor: The viscosity of the mixed liquid is lower than both the viscosities of the first agent and the second agent.

6. Dripping

A first agent and a second agent were mixed with a gas at a predetermined ratio, and 80 g of the mixed liquid was applied to the whole head of a commercially available wig with hand wearing a glove. Thereafter, the wig was allowed to stand for 30 minutes, washed with water, and dried. Dripping thereupon was evaluated based on the following criteria.

Excellent: There is no dripping during the leaving time.
Acceptable: There is slight dripping.
Poor: There is much dripping.

7. Comprehensive Evaluation

In the field of hair cosmetics, particularly in the field of hair dye and decolorant, the hair cosmetic is required to have high performance in all of dyeability of the hair dye (or decoloring property of the decolorant), touch feeling, applicability, mixability and thickening property, and dripping. Therefore, comprehensive evaluation was conducted as follows.

Excellent: All of five items of dyeability (or decoloring property), touch feeling, applicability, mixability and thickening property, and dripping are excellent.

Good: All of the five items are excellent or good, and at least one of the five items is good.

Acceptable: All of the five items are excellent, good or acceptable, and at least one of the five items is acceptable.

Poor: All of the five items are excellent, good, acceptable or poor, and at least one of the five items is poor.

TABLE 1

|  | Components | Examples |  |  |  |  |  | Comparative Examples |  |
|---|---|---|---|---|---|---|---|---|---|
|  |  | 1 | 2 | 3 | 4 | 5 | 6 | 1 | 2 |
| First Agent | propylene glycol | 5 | 5 | 5 | 5 | 5 | 5 | 5 | 5 |
|  | aqueous ammonia (28%) |  |  | 5 | 5 | 5 | 5 |  |  |
|  | monoethanolamine | 10 | 10 | 3 | 3 | 3 | 3 | 10 | 10 |
|  | ammonium hydrogen carbonate |  |  | 1 | 1 | 1 | 1 |  |  |
|  | tetrasodium edetate tetrahydrate | 0.2 | 0.2 | 0.2 | 0.2 | 0.2 | 0.2 | 0.2 | 0.2 |
|  | ascorbic acid | 0.3 | 0.3 | 0.3 | 0.3 | 0.3 | 0.3 | 0.3 | 0.3 |
|  | sodium sulfite | 0.4 | 0.4 | 0.4 | 0.4 | 0.4 | 0.4 | 0.4 | 0.4 |
|  | 2,5-diaminotoluene sulfate | 1.55 | 1.55 | 0.44 | 0.44 | 0.44 | 1.55 | 1.55 | 1.55 |
|  | p-aminophenol | 0.4 | 0.4 | 0.22 | 0.22 | 0.22 | 0.4 | 0.4 | 0.4 |
|  | m-aminophenol | 0.13 | 0.13 | 0.11 | 0.11 | 0.11 | 0.13 | 0.13 | 0.13 |
|  | resorcin | 0.91 | 0.91 | 0.27 | 0.27 | 0.27 | 0.91 | 0.91 | 0.91 |
|  | 5-amino-o-cresol | 0.15 | 0.15 | 0.07 | 0.07 | 0.07 | 0.15 | 0.15 | 0.15 |
|  | purified water | q.s. | q.s. | q.s. | q.s. | q.s. | q.s. | q.s. | q.s. |
|  | total | 100 | 100 | 100 | 100 | 100 | 100 | 100 | 100 |
| Second Agent | stearyl trimethyl ammoium chloride (80%) | 1 | 1.5 | 1 | 1 | 1 | 1 | 1 | 1 |
|  | cetanol | 4 | 1.5 | 4 | 4 | 4 | 4 | 4 | 4 |
|  | polyoxyethylene (12) cetostearyl ether |  |  |  | 1 |  |  |  |  |
|  | polyoxyethylene (30) cetostearyl ether | 6 | 1.5 | 6 | 5 |  | 6 | 6 | 6 |
|  | polyoxyethylene (40) cetyl ether |  |  |  |  | 6 |  |  |  |
|  | liquid paraffin | 3 | 1.5 | 3 | 3 | 3 |  |  |  |
|  | squalane |  |  |  |  |  | 3 |  |  |
|  | isopropyl palmitate |  |  |  |  |  |  | 3 |  |
|  | macadamia nut oil |  |  |  |  |  |  |  | 3 |
|  | glycerin | 2 | 1.5 | 2 | 2 | 2 | 2 | 2 | 2 |
|  | polychlorinated dimethylinethylene piperidinium liquid (40%) | 0.5 | 0.5 | 0.5 | 0.5 | 0.5 | 0.5 | 0.5 | 0.5 |
|  | hydroxyethane diphosphonic acid liquid (60%) | 0.25 | 0.25 | 0.25 | 0.25 | 0.25 | 0.25 | 0.25 | 0.25 |
|  | phenoxyethanol | 0.25 | 0.25 | 0.25 | 0.25 | 0.25 | 0.25 | 0.25 | 0.25 |
|  | sodium pyrophosphate (for adjustment of pH to 3) | q.s. | q.s. | q.s. | q.s. | q.s. | q.s. | q.s. | q.s. |
|  | hydrogen peroxide water (35% aqueous solution) | 16 | 16 | 16 | 16 | 16 | 16 | 16 | 16 |
|  | purified water | q.s. | q.s. | q.s. | q.s. | q.s. | q.s. | q.s. | q.s. |
|  | total | 100 | 100 | 100 | 100 | 100 | 100 | 100 | 100 |
|  | mixing ratio | 1:2 | 1:2 | 1:2 | 1:2 | 1:2 | 1:2 | 1:2 | 1:2 |
| Results | 1. Dyeability | ◎ | ◎ | ◎ | ◎ | ◎ | ◎ | ◎ | ◎ |
|  | 2. Touch feeling | ◎ | ◎ | ◎ | ◎ | ◎ | ◎ | ○ | Δ |
|  | 3. Applicability | ◎ | ◎ | ◎ | ◎ | ◎ | ◎ | ◎ | ◎ |
|  | 4. Mixability and thickening property | ◎ | ◎ | ◎ | ◎ | ◎ | ◎ | Δ | Δ |
|  | 5. Dripping | ◎ | ◎ | ◎ | ◎ | ◎ | ◎ | X | X |
|  | Comprehensive evaluation | ◎ | ◎ | ◎ | ◎ | ◎ | ◎ | X | X |

◎: Excellent,
○: Good,
Δ: Acceptable,
X: Poor

TABLE 2

| | Components | Examples 7 | 8 | 9 | 10 | 11 | 12 | Comparative Examples 3 | 4 |
|---|---|---|---|---|---|---|---|---|---|
| First Agent | propylene glycol | 5 | 5 | 5 | 5 | 5 | 5 | 5 | 5 |
| | aqueous ammonia (28%) | | | | | | | | |
| | monoethanolamine | 10 | 10 | 10 | 10 | 10 | 10 | 10 | 10 |
| | ammonium hydrogen carbonate | | | | | | | | |
| | tetrasodium edetate tetrahydrate | 0.2 | 0.2 | 0.2 | 0.2 | 0.2 | 0.2 | 0.2 | 0.2 |
| | ascorbic acid | 0.3 | 0.3 | 0.3 | 0.3 | 0.3 | 0.3 | 0.3 | 0.3 |
| | sodium sulfite | 0.4 | 0.4 | 0.4 | 0.4 | 0.4 | 0.4 | 0.4 | 0.4 |
| | 2,5-diaminotoluene sulfate | 1.55 | 1.55 | 1.55 | 1.55 | 1.55 | 1.55 | 1.55 | 1.55 |
| | p-aminophenol | 0.4 | 0.4 | 0.4 | 0.4 | 0.4 | 0.4 | 0.4 | 0.4 |
| | m-aminophenol | 0.13 | 0.13 | 0.13 | 0.13 | 0.13 | 0.13 | 0.13 | 0.13 |
| | resorcin | 0.91 | 0.91 | 0.91 | 0.91 | 0.91 | 0.91 | 0.91 | 0.91 |
| | 5-amino-o-cresol | 0.15 | 0.15 | 0.15 | 0.15 | 0.15 | 0.15 | 0.15 | 0.15 |
| | purified water | q.s. | q.s. | q.s. | q.s. | q.s. | q.s. | q.s. | q.s. |
| | total | 100 | 100 | 100 | 100 | 100 | 100 | 100 | 100 |
| Second Agent | stearyl trimethyl ammoium chloride (80%) | 1 | 1 | 1 | 1 | 1 | 1 | 1 | 1 |
| | cetanol | 4 | 4 | 4 | 4 | 4 | 4 | 4 | 4 |
| | polyoxyethylene (12) cetostearyl ether | | 1.5 | 0.3 | 0.3 | 0.3 | 1.4 | 0.2 | |
| | polyoxyethylene (30) cetostearyl ether | 6 | 6 | 7.5 | 1.5 | 1.5 | 1.5 | 10 | 1 |
| | polyoxyethylene (40) cetyl ether | | | | | | | | |
| | liquid paraffin | | | 3 | 3 | 3 | 3 | 3 | 3 |
| | octyl dodecyl myristate | 3 | | | | | | | |
| | isocetyl isostearate | | 3 | | | | | | |
| | macadamia nut oil | | | | | | | | |
| | glycerin | 2 | 2 | 2 | 2 | 2 | 2 | 2 | 2 |
| | polychlorinated dimethylmethylene piperidinium liquid (40%) | 0.5 | 0.5 | 0.5 | 0.5 | 0.5 | 0.5 | 0.5 | 0.5 |
| | hydroxyethane diphosphonic acid liquid (60%) | 0.25 | 0.25 | 0.25 | 0.25 | 0.25 | 0.25 | 0.25 | 0.25 |
| | phenoxyethanol | 0.25 | 0.25 | 0.25 | 0.25 | 0.25 | 0.25 | 0.25 | 0.25 |
| | sodium pyrophosphate (for adjustment of pH to 3) | q.s. | q.s. | q.s. | q.s. | q.s. | q.s. | q.s. | q.s. |
| | hydrogen peroxide water (35% aqueous solution) | 16 | 16 | 16 | 16 | 16 | 16 | 16 | 16 |
| | purified water | q.s. | q.s. | q.s. | q.s. | q.s. | q.s. | q.s. | q.s. |
| | total | 100 | 100 | 100 | 100 | 100 | 100 | 100 | 100 |
| | mixing ratio | 1:2 | 1:2 | 1:2 | 1:2 | 1:1 | 1:1.5 | 1:2 | 1:2 |
| Results | 1. Dyeability | ◎ | ◎ | ◎ | ◎ | ◎ | ◎ | ◎ | ◎ |
| | 2. Touch feeling | ◎ | ◎ | ◎ | ◎ | ◎ | ◎ | ○ | ◎ |
| | 3. Applicability | ◎ | ◎ | ◎ | ◎ | ◎ | ◎ | ◎ | ◎ |
| | 4. Mixability and thickening property | ◎ | ◎ | ○ | ○ | ○ | ○ | Δ | Δ |
| | 5. Dripping | ◎ | ◎ | ◎ | ◎ | ◎ | ◎ | X | ◎ |
| | Comprehensive evaluation | ◎ | ◎ | ○ | ○ | ○ | ○ | X | Δ |

◎: Excellent,
○: Good,
Δ: Acceptable,
X: Poor

TABLE 3

| | Components | Examples 13 | 14 | 15 |
|---|---|---|---|---|
| First Agent | propylene glycol | 5 | | 5 |
| | aqueous ammonia (28%) | | | |
| | monoethanolamine | 10 | 10 | 10 |
| | ammonium hydrogen carbonate | | | |
| | tetrasodium edetate tetrahydrate | 0.2 | 0.2 | 0.2 |
| | ascorbic acid | 0.3 | 0.3 | 0.3 |
| | sodium sulfite | 0.4 | 0.4 | 0.4 |
| | 2,5-diaminotoluene sulfate | | 1.55 | 1.55 |
| | p-aminophenol | | 0.4 | 0.4 |
| | m-aminophenol | | 0.13 | 0.13 |
| | resorcin | | 0.91 | 0.91 |
| | 5-amino-o-cresol | | 0.15 | 0.15 |
| | purified water | q.s. | q.s. | q.s. |
| | total | 100 | 100 | 100 |
| Second Agent | stearyl trimethyl ammoium chloride (80%) | 1 | 1 | 1 |

TABLE 3-continued

|  | | Examples | | |
|---|---|---|---|---|
| Components | | 13 | 14 | 15 |
| | cetanol | 4 | 4 | 4 |
| | polyoxyethylene (12) cetostearyl ether | | | |
| | polyoxyethylene (30) cetostearyl ether | 6 | 6 | 6 |
| | polyoxyethylene (40) cetyl ether | | | |
| | liquid paraffin | 3 | 3 | 3 |
| | glycerin | 2 | | |
| | polychlorinated dimethylmethylene piperidinium liquid (40%) | 0.5 | 0.5 | 0.5 |
| | hydroxyethane diphosphonic acid liquid (60%) | 0.25 | 0.25 | 0.25 |
| | phenoxyethanol | 0.25 | 0.25 | 0.25 |
| | sodium pyrophosphate (for adjustment of pH to 3) | q.s. | q.s. | q.s. |
| | hydrogen peroxide water (35% aqueous solution) | 16 | 16 | 16 |
| | purified water | q.s. | q.s. | q.s. |
| | total | 100 | 100 | 100 |
| | mixing ratio | 1:2 | 1:2 | 1:2 |
| Results | 1. Dyeability | ◎ | ◎ | ◎ |
| | 2. Touch feeling | ◎ | ◎ | ◎ |
| | 3. Applicability | ◎ | ◎ | ◎ |
| | 4. Mixability and thickening property | ◎ | ○ | ○ |
| | 5. Dripping | ◎ | ◎ | ◎ |
| | Comprehensive evaluation | ◎ | ○ | ○ |

◎: Excellent, ○: Good, Δ: Acceptable, X: Poor

TABLE 4

|  | | Comparative Examples | |
|---|---|---|---|
| Components | | 5 | 6 |
| First Agent | sodium polyxyethylene (2) laurylether sulfate (28%) | 8 | 25 |
| | hexyldecanol | 3 | |
| | propylene glycol | 4 | 9 |
| | coconut oil fatty acid diethanolamine | | 10 |
| | oleic acid | | 5 |
| | ethanol | | 10 |
| | aqueous ammonia (28%) | 7 | 6.5 |
| | monoethanolamine | 1 | 1 |
| | tetrasodium edetate tetrahydrate | 0.2 | 0.2 |
| | sodium sulfite | 0.4 | 0.4 |
| | ascorbic acid | 0.3 | 0.3 |
| | p-phenylendiamine | 0.35 | 0.35 |
| | m-aminophenol | 0.03 | 0.03 |
| | resorcin | 0.3 | 0.3 |
| | purified water | q.s. | q.s. |
| | total | 100 | 100 |
| Second Agent | sodium polyxyethylene (2) laurylether sulfate | 1.8 | 2 |
| | cetanol | 1 | 1 |
| | acrylic acid-alkyl methacrylate copolymer | 1 | |
| | hydroxyethane diphosphonic acid liquid (60%) | 0.25 | 0.25 |
| | phenoxyethanol | 0.25 | 0.25 |
| | sodium pyrophosphate (for adjustment of pH to 3) | q.s. | q.s. |
| | phosphoric acid (for adjustment of pH to 3) | q.s. | q.s. |
| | hydrogen peroxide water (35% aqueous solution) | 16 | 16 |
| | purified water | q.s. | q.s. |
| | total | 100 | 100 |
| | mixing ratio | 1:1 | 1:1 |

TABLE 4-continued

|  | | Comparative Examples | |
|---|---|---|---|
| Components | | 5 | 6 |
| Results | 1. Dyeability | ◎ | ◎ |
| | 2. Touch feeling | Δ | X |
| | 3. Applicability | ○ | ◎ |
| | 4. Mixability and thickening property | ◎ | ◎ |
| | 5. Dripping | ◎ | Δ |
| | Comprehensive evaluation | Δ | X |

◎: Excellent, ○: Good, Δ: Acceptable, X: Poor

TABLE 5

| | Viscosity (mPa·s) | | |
|---|---|---|---|
| | First Agent | Second Agent | After Mixing |
| Example 3 | 100 or less | 5720 | 7190 |
| Example 4 | 100 or less | 5740 | 7630 |
| Example 6 | 100 or less | 5760 | 7160 |
| Example 9 | 100 or less | 280 | 4260 |
| Example 13 | 100 or less | 5720 | 6850 |
| Example 14 | 100 or less | 5290 | 6470 |
| Example 15 | 100 or less | 5290 | 6680 |
| Comparative Example 3 | 100 or less | 230 | 620 |

The first agent and the second agent of Example 4 were mixed with each other immediately before use in the mixing ratio shown in Table 1 according to mixing methods A to C. The viscosity of the resulting mixed liquid is shown in Table 6.

Mixing method A: Into a bottle having a diameter of 5 cm and a height of 13 cm, 30 g of the first agent and 60 g of the second agent were placed, the bottle was closed with a lid, and the bottle was shaken at an amplitude of 30 cm each 30 times in a horizontal direction and a vertical direction at a rate of about once per second to mix the agents.

Mixing method B: Into a jar having a diameter of 7.5 cm and a height of 5 cm, 30 g of the first agent and 60 g of the second agent were placed, the jar was closed with a lid, and the jar was shaken at an amplitude of 30 cm each 30 times in a horizontal direction and a vertical direction at a rate of about once per second to mix the agents.

Mixing method C: Into a cup were placed 30 g of the first agent and 60 g of the second agent, and the agents were stirred using a glass bar to mix.

TABLE 6

| | Viscosity (mPa·s) | | | | |
|---|---|---|---|---|---|
| | | | Mixture | | |
| | First Agent | Second Agent | Mixing method A | Mixing method B | Mixing method C |
| Example 4 | 100 or less | 5720 | 7630 | 7230 | 2500 |

As shown in Table 6, when the hair cosmetic of the present invention is mixed with a gas by, for example, the Mixing method A or Mixing method B, sufficient thickening of the hair cosmetic is achieved, although the method of mixing with a gas is not particularly limited. In the case where the hair cosmetic is not mixed with a gas as in Mixing method C, thickening is not achieved.

What is claimed is:

1. A hair cosmetic comprising:
    (A) 0.1 wt % to 5 wt % of a cationic surfactant based on the total weight of the hair cosmetic;
    (B) 0.1 wt % to 10 wt % of a nonionic surfactant based on the total weight of the hair cosmetic;
    (C) 0.1 wt % to 10 wt % of a higher alcohol based on the total weight of the hair cosmetic;
    (D) an oil having an IOB value of 0.1 or lower; and
    (E) water,
which is used after being mixed with a gas to be thickened, wherein the ratio of the total content of the surfactants (A) and (B) relative to the content of (C) the higher alcohol is 0.6 to 2.5.

2. The hair cosmetic according to claim 1, further comprising (F) a water-soluble polyhydric alcohol.

3. The hair cosmetic according to claim 1, wherein the hair cosmetic is a hair dye or a decolorant.

4. The hair cosmetic according to claim 3, wherein the hair cosmetic is a two-pack type hair dye or decolorant comprising a first agent containing an alkali agent and a second agent containing an oxidizing agent.

5. The hair cosmetic according to claim 4, wherein (A) to (E) are contained in the second agent.

6. The hair cosmetic according to claim 1, wherein the viscosity before being mixed with a gas is 8000 mPa·s or less, the viscosity after being mixed with a gas is 2000 mPa·s to 12000 mPa·s, and the hair cosmetic is thickened at a thickening rate of 10% or more by being mixed with a gas.

7. A method of using a hair cosmetic, in which the hair cosmetic according to claim 6 is thickened by being mixed with a gas, and applied to the hair.

* * * * *